(12) United States Patent
Brown et al.

(10) Patent No.: US 10,130,091 B2
(45) Date of Patent: *Nov. 20, 2018

(54) AGROCHEMICAL EMULSIFIABLE CONCENTRATE FORMULATION

(71) Applicant: Huntsman Corporation Australia Pty Limited, Brooklyn (AU)

(72) Inventors: Rowan Brown, Ascot Vale (AU); Marie Giansiracusa, Reservoir (AU); Dilek Saylik, Meadow Heights (AU); Martin Edmond Doyle, Ascot Vale (AU); Andrew F Kirby, Footscray (AU)

(73) Assignee: HUNTSMAN PETROCHEMICAL LLC, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/377,261

(22) PCT Filed: Feb. 25, 2013

(86) PCT No.: PCT/AU2013/000165
§ 371 (c)(1),
(2) Date: Aug. 7, 2014

(87) PCT Pub. No.: WO2013/126948
PCT Pub. Date: Sep. 6, 2013

(65) Prior Publication Data
US 2015/0342180 A1    Dec. 3, 2015

(30) Foreign Application Priority Data

Feb. 27, 2012 (AU) ................ 2012900730

(51) Int. Cl.
| | | |
|---|---|---|
| *A01N 33/18* | (2006.01) |
| *A01N 25/02* | (2006.01) |
| *A01N 25/04* | (2006.01) |
| *A01N 25/30* | (2006.01) |
| *A01N 53/00* | (2006.01) |

(52) U.S. Cl.
CPC ............ *A01N 25/02* (2013.01); *A01N 25/04* (2013.01); *A01N 25/30* (2013.01); *A01N 33/18* (2013.01); *A01N 53/00* (2013.01)

(58) Field of Classification Search
CPC ........ A01N 33/18; A01N 25/02; A01N 25/04; A01N 25/22; A01N 25/30
See application file for complete search history.

(56) References Cited

U.S. PATENT DOCUMENTS

| | | | |
|---|---|---|---|
| 5,444,078 A | 8/1995 | Yu et al. | |
| 5,472,700 A * | 12/1995 | Staetz | A01N 53/00 424/405 |
| 5,846,997 A | 12/1998 | Sirinyan et al. | |
| 6,635,663 B1 | 10/2003 | Zen | |
| 2004/0082476 A1 | 4/2004 | Haesslin et al. | |
| 2007/0244011 A1 * | 10/2007 | Gioia | A01N 33/18 504/347 |
| 2009/0005246 A1 * | 1/2009 | Schneider | A01N 43/90 504/108 |
| 2011/0045975 A1 | 2/2011 | Ehr et al. | |

FOREIGN PATENT DOCUMENTS

| | | |
|---|---|---|
| JP | 2009-173569 A | 8/2009 |
| JP | 2009-173596 A | 8/2009 |
| WO | 2005074683 A | 8/2005 |

* cited by examiner

*Primary Examiner* — John Pak
*Assistant Examiner* — Nathan W Schlientz
(74) *Attorney, Agent, or Firm* — Huntsman Petrochemical LLC; Edward Korompai

(57) ABSTRACT

An agrochemical emulsifiable concentrate (EC) formulation comprising at least one agrochemical active ingredient; at least one surfactant emulsifier; optionally, a stabilizer; and a primary solvent system, wherein the solvent system is selected from benzyl acetate or a combination of benzyl acetate and at least one substantially water-immiscible co-solvent.

15 Claims, No Drawings

AGROCHEMICAL EMULSIFIABLE CONCENTRATE FORMULATION

CROSS-REFERENCE TO RELATED APPLICATIONS

This application is the National Phase of International Application PCT/AU2013/000165 filed Feb. 25, 2013 which designated the U.S. and which claims priority to Australia Application Serial No. 2012900730 filed Feb. 27, 2012. The noted applications are incorporated herein by reference.

FIELD OF THE INVENTION

The invention relates to an emulsifiable concentrate (EC) formulation of agrochemical active ingredients utilising an improved primary solvent system, wherein the solvent system is selected from benzyl acetate or a combination of benzyl acetate and at least one substantially water-immiscible co-solvent. More preferably, the improved solvent system provides a substantially storage-stable and dilution-stable emulsifiable concentrate (EC) formulation.

BACKGROUND OF THE INVENTION

In the art of formulating agrochemicals, it is often necessary to dissolve the agrochemical active ingredient in a solvent and then dilute it in a larger volume of water in order for it to be broadcast in the form of a fine spray. In still other cases, it is necessary to dilute the active ingredient in a solution and apply it to a seed or other solid carrier. While some active ingredients, which are usually in the form of a salt, can be simply dissolved and then diluted in water, the majority of agrochemical active ingredients are hydrophobic and therefore not water-soluble. In the case of active ingredients which are not water-soluble, it is normally necessary to dissolve the formulation in a water-immiscible solvent and add surfactants, so that the solution will form an oil-in-water emulsion when added to water. Such a formulation is called an Emulsifiable Concentrate (EC) formulation. Alternatively, the water-immiscible solution of an active ingredient can be pre-emulsified in water in a concentrated form. Such a formulation is called an Emulsion-in-Water (EW) formulation. A special sub-class of EW formulations is the so-called Microemulsion (ME) formulation, where the emulsion particle size is such that the formulation does not scatter light and has a clear or translucent appearance.

Water-immiscible solvents commonly used for EC and EW formulations include, but are not limited to, aromatic hydrocarbons such as the SOLVESSO® series, paraffinic hydrocarbons such as the EXXSOL® range, ester solvents such as the EXXATE© range, all of which are manufactured by EXXONMOBIL, and ester solvents such as methyl-oleate. Other solvents which are water-immiscible at high concentration include cyclic hydrocarbons, such as cyclohexanone and isophorone.

In more recent times, solvents which exhibit improved toxicity and reduced flammability profiles have been used. These include the dibasic ester solvents of long chain di-acids having from 8-16 carbon units, which are usually methyl ester derivatives, and fatty acid amide solvents, examples of which are the dimethylamide and morpholineamide derivatives of $C_6$-$C_{16}$ fatty acids. Mono-alkylene carbonates, such as ethylene, propylene and butylene carbonates, also find use as co-solvents, although they can generally be considered as water-miscible when used at most practical end-use dilution rates.

Combinations of water-immiscible solvents with highly polar water-miscible co-solvents such as N-methyl pyrrolidinone, dimethylsulphoxide, dimethylisosorbide, monoethylene glycol, monopropylene glycol and various glycol ethers, have been used in the past to achieve physical stability of the EC formulation, particularly if crystallisation of the active ingredient occurs at below ambient temperature. However, the use of such solvent combinations often leads to the problem of crystallisation in the diluted formulation.

There is a particular need for low toxicity and low flammability polar solvents, which can dissolve the more polar active ingredients, but which are not so polar as to have significant water-solubility resulting in crystallisation of the active ingredient upon dilution. In particular, it is desirable to be able to dissolve certain problematic agrochemical active ingredients in high concentration for use in emulsifiable concentrate formulations. High concentration EC formulations have significant advantages in costs, shipping and handling. Such active ingredients include, but are not limited to, dinitroaniline herbicides such as trifluralin, pendimethalin, benfluralin and butralin; diphenylether herbicides such as oxyfluorfen and aclonifen; phenoxypropionate herbicides such as metamifop; synthetic pyrethroid insecticides such as deltamethrin, bifenthrin, zeta-cypermethrin, gamma- and lambda-cyhalothrin and alpha-cypermethrin; organophosphate insecticides such as phosmet and omethoate; and various acaricides including amitraz, buprofezin and pyridaben.

While many of the dibasic ester and fatty amide-based solvents can dissolve some of the active ingredients in the polarity range of these solvents, there are limitations on the amount of active ingredient that can be dissolved. Further, not all of these classes of solvents have desirable toxicity profiles. In addition, significant effort and expense can be involved in the manufacture and, in particular, the purification of these solvents.

While mono-short chain alkylene carbonate solvents have an overall excellent toxicity profile and reduced flammability, their major limitation is that they are generally water-miscible upon dilution and do not fully dissolve many of the active ingredients described above.

The use of benzyl acetate as a solvent for agrochemical active ingredients is known. Japanese Patent Application JP 2009173569A teaches the use of benzyl acetate and butylacetoacetate in combination with a water-miscible co-solvent, 1,3-dimethyl-2-imidazolidinone and an aromatic hydrocarbon to prepare emulsion compositions of various hydrophobic agrochemical active ingredients up to 50% weight/volume. International Patent Publication No. WO 2011/017480 teaches benzyl acetate as a suitable solvent for dissolving certain active ingredients in preparation for forming microcapsule compositions.

There is, however, still a need for water-immiscible solvent combinations, having an improved toxicity and flammability profile.

The present invention seeks to provide an improved solvent system for high concentration emulsifiable concentrate formulations that at least ameliorates certain disadvantages associated with previously known solvent systems.

SUMMARY OF THE INVENTION

In order for a solvent to be effective for use in an agrochemical formulation, such as an EC or EW formulation, it is necessary for the active ingredient to be sufficiently soluble, such that no crystallisation thereof is observed in the temperature range of from 0° C. to 54° C. and more preferably, in the temperature range of from −5° C. to 54° C. A number of polar water-miscible co-solvents have been found to be useful with problematic agrochemical active ingredients in achieving stability of the formulation concentrate to crystallisation. Such solvents include, but are not limited to, N-methylpyrrolidinone (NMP), dimethylsulphoxide (DMSO), dimethylformamide (DMF), dimethylisosorbide (DMI), isophorone, acetophenone and cyclohexanone. However, some of these solvents are undesirable because of their toxicity profile alone. A major difficulty with using these types of polar solvents is that while the problem of crystallisation can be solved, the stability of the diluted formulation and the resulting emulsion to crystallisation of the active ingredient is inadequate.

The present inventors have now surprisingly found that when benzyl acetate is used on its own or in combination with at least one other substantially water-immiscible co-solvent/s, described herein as the primary solvent system, storage-stable and dilution-stable formulations of certain problematic active ingredients can be achieved at higher loadings than could previously be achieved with alternative solvent combinations.

According to one aspect of the present invention, there is provided an agrochemical emulsifiable concentrate (EC) formulation comprising at least one agrochemical active ingredient; at least one surfactant emulsifier; optionally, a stabiliser; and a primary solvent system, wherein the solvent system is selected from benzyl acetate or a combination of benzyl acetate and at least one substantially water-immiscible co-solvent. The benzyl actetate is preferably used with the substantially water-immiscible co-solvent in a mixing ratio range of from 10:90 to 90:10, more preferably in the mixing ratio range of from 40:60 to 80:20, as the primary solvent system.

The at least one substantially water-immiscible co-solvent is preferably selected from the group of aromatic hydrocarbons, aliphatic hydrocarbons, alkylesters and alkenyl esters. It has been found that when benzyl acetate is used in combination with aromatic hydrocarbon solvents, such a solvent system is able to afford formulations of a higher than normally used concentration, which are both stable in concentrate form and stable to crystallisation upon dilution in water.

In a preferred form, the active ingredient when present in the concentrate formulation is not fully soluble in the substantially water-immiscible co-solvent when the solvent is used on its own after storage at 0° C. with crystal seeding.

According to another preferred aspect of the invention, the primary solvent system comprises benzyl acetate used on its own.

The active ingredient used in the EC formulation is preferably selected from a pesticide or a herbicide, such as dinitroaniline herbicides; diphenylether herbicides; synthetic pyrethroid insecticides; phenoxypropionate herbicides; organophosphate insecticides; or various acaricides including amitraz, buprofezin and pyridaben; or mixtures thereof.

The at least one active ingredient is preferably selected from trifluralin, pendimethalin, butralin, benfluralin, oxyfluorfen, aclonifen, deltamethrin, bifenthrin, lambda- and gamma-cyhalothrin, alpha- and zeta-cypermethrin, metamifop, phosmet, omethoate, amitraz, buprofezin, triadimefon and pyridaben; or mixtures thereof.

In a more preferred form, the active ingredient is trifluralin, which is present in a concentration of greater than 500 g/L or greater than 50% weight/volume. In a further more preferred form, the active ingredient is bifenthrin, which is present in a concentration of greater than 100 g/L.

In one aspect, the formulation of the present invention further comprises at least one water-miscible co-solvent, wherein the water-miscible co-solvent which may be present as a component of another solvent, is however not required to dissolve the active ingredient.

The at least one surfactant emulsifier used in the EC formulation is selected from the group comprising alkoxylated alcohols; alkoxylated alkylphenols; ethoxylated fatty acids; ethoxylated vegetable oils; ethoxylated tristyrylphenol; fatty acid esters of sorbitol and ethoxylated derivatives thereof ethoxylated amines and condensates of glycerol; sulfonated alkylbenzenes in the range $C_{11}$-$C_{16}$ and salts thereof; alkylether sulphates; alkyletherphosphates; alkylphenoletherphosphates; or combinations thereof; salts of phosphate esters of ethoxylated tristyrylphenol; salts of sulphated ethers of ethoxylated tristyrylphenol; or a catanionic system, wherein a cationic amine is present in combination with an alkylsulphonate, an alkylethersulphonate, an ether sulphate, or an ether phosphate such as an alkyletherphosphate.

The EC formulation of the present invention preferably further comprises a stabiliser, selected from butylated hydroxytoluene (BHT) and epoxidized soybean oil (ESBO). The stabiliser is preferably present in a concentration of up to 3% weight/volume and is more preferably added to the formulation once the active ingredient is dissolved in the solvent system.

Combinations of benzyl acetate with other substantially non-polar solvents have been found to have good utility with certain crystalline active ingredients including, but not limited to, dinitroaniline herbicides such as trifluralin and pendimethalin; diphenylether herbicides such as oxyfluorfen; and synthetic pyrethroid insecticides such as deltamethrin and bifenthrin. It has been found that these active ingredients can be formulated at a high enough loading to produce stable and more commercially desirable formulations, while at the same time maintaining an acceptable toxicity profile and low flammability.

The scope of the present invention also extends to methods of formulating agrochemical active ingredients without using either further harmful or high odour solvents.

In one preferred aspect, the present invention is directed to the method of making an EC formulation comprising at least one agrochemical active ingredient. The method comprises the following steps: firstly, forming a mixture comprising the agrochemical active ingredient, the substantially water-immiscible co-solvent and benzyl acetate and then secondly, adding a suitable surfactant emulsifier and/or stabilizer to the mixture. The mixture is preferably formed by forming a mixture comprising the agrochemical active ingredient and benzyl acetate and then adding the substantially water-immiscible co-solvent; or by forming a mixture comprising the agrochemical active ingredient and a substantially water-immiscible co-solvent and then adding benzyl acetate; or by forming a mixture comprising the agrochemical active ingredient and a combination of benzyl acetate and a substantially water-immiscible co-solvent; or by combining the agrochemical active ingredient, benzyl acetate and a substantially water-immiscible co-solvent.

The mixing, preferably by dissolving, of the active ingredient in the substantially water-immiscible co-solvent is preferably achieved in the presence of heating up to 60° C.

In another preferred aspect, the present invention is directed to the method of making an emulsion-in-water (EW) formulation comprising at least one agrochemical active ingredient, wherein the method comprises the same steps for making an EC formulation as described above, followed by contacting the composition with water.

A further advantage in using benzyl acetate solvent is that it is relatively cheap compared to many of the specialty solvents, which may be able to achieve high loading formulations of similar strength. Benzyl acetate also has the advantage of having a low odour.

Further, it has been found that benzyl acetate together with other solvents can usefully be emulsified together with one or more desired active ingredients with conventional surfactants known to be useful as emulsifiers for agrochemical formulations, such as EC formulations. That is, the benzyl acetate solvent system does not require any specialized emulsifier systems to achieve a stable emulsion upon dilution.

DESCRIPTION OF THE PREFERRED EMBODIMENT

It can be seen from the physical properties of benzyl acetate, which are summarized in Table 1 below, that this solvent shows relatively low volatility and flammability.

TABLE 1

| Physical Properties of Benzyl Acetate | Result |
|---|---|
| Boiling point, ° C. | 212 |
| Melting Point, ° C. | −51 |
| Density, g/cm$^3$ | 1.04 |
| Solubility in water, % w/w | <1 |
| Viscosity @ 45° C., cP | 1.4 |
| Flashpoint, ° C. | 90 |
| Auto-ignition temperature, ° C. | 460 |

The toxicological properties of benzyl acetate are summarized in Table 2 as follows:

TABLE 2

| Toxicity of Benzyl Acetate | Result |
|---|---|
| Acute oral toxicity, LD50 (est) mouse, mg/kg | 830 |
| Acute dermal toxicity, LD50 (est) rabbit, mg/kg | >500 |
| TLV as TWA, ppm | 10 |

Benzyl acetate shows relatively low toxicity.

An EC formulation is preferably diluted into water at rates ranging from 0.1 to 20% w/v, and more preferably, in the range of from 0.5 to 5% w/v. In order for an EC formulation to be useable, it should not show crystallisation in the diluted emulsion before spraying and it must be stable for the time allowed between dilution and spraying. Typical time standards for dilution stability of active ingredients are set out by the Food and Agriculture Organization of the United Nations (FAO) and may be found in the various technical monographs prepared by them. For emulsion stability, it is expected that a formulation upon dilution would be substantially free of crystals for more than 2 hours, and more preferably, for more than 24 hours.

Accordingly, it has been surprisingly found that if a sufficient amount of benzyl acetate is used in combination with at least one substantially water-immiscible co-solvent, such as, for example, the aromatic hydrocarbon solvents, as the primary solvent system, sufficient solubility toward certain crystalline active ingredients is afforded to maintain stability of the formulation concentrate, whilst also affording stability toward crystallisation on dilution in water.

The term "primary solvent" used in the primary solvent system of the present invention is a solvent which must be present to dissolve the active ingredient. The term "non-primary solvent" as used herein is a solvent which may optionally also be present in the solvent system, but which is not required for the purposes of dissolving the active ingredient. Non-primary solvents may incidentally be present in emulsifier blends or as an agent which adds additional features or characteristics such as colour, stability or viscosity to the overall formulation. In general, if less than about 10% of a non-primary solvent is present, such a solvent will not function as part of the primary solvent system.

The water-immiscible co-solvents useful in the present invention preferably include, but are not limited to, aromatic hydrocarbons such as those of the SOLVESSO® series manufactured by EXXONMOBIL, which consists mainly of alkyl substituted benzenes and naphthalenes; paraffinic hydrocarbons such as the EXXSOL® range; and ester solvents such as the EXXATE® range, all manufactured by EXXONMOBIL; xylenes, toluene and various $C_9$ aromatic distillation cuts. Other water-immiscible co-solvents further preferably include fatty acids and fatty acid methyl esters. In order to be considered water-immiscible, the solvent should have insufficient water-solubility at the anticipated dilution rates of the EC formulation, which are typically greater than 1 part in 1000.

The present invention may further comprise one or more substantially water-miscible co-solvents as a non-primary solvent, so long as such a solvent is not present in sufficient quantity to re-induce crystallisation of the active ingredient upon dilution in water. Typically, the substantially water-miscible co-solvent is present at no more than 10% w/v in the total formulation used.

The terms "agrochemical active" or "agrochemically active" as used herein also cover all the related uses of the EC formulations, such as in animal health, public health, water treatment, wood treatment, home garden and domestic vector control. The agrochemical active ingredients useful in the present invention preferably include those as listed in the Pesticide Manual of the British Crop Protection Council (14$^{th}$ Edition), which are soluble in substantially water-immiscible solvents.

The active ingredient/s and formulation/s, where there is a higher concentration EC formulation than would otherwise be expected in the absence of benzyl acetate, further preferably include/s, but is/are not limited to: dinitroaniline herbicides such as trifluralin, present at a concentration greater than 500 g/L; pendimethalin present at a concentration greater than 330 g/L; diphenylether herbicides, such as oxyfluorfen, present at a concentration of 240 g/L or more; and synthetic pyrethroid insecticides such as deltamethrin and bifenthrin, separately present at a concentration of 100 g/L or more; or combinations of more than one of the afore-mentioned active ingredients.

The active ingredient of the present invention preferably includes any ingredient which falls within the polarity range, where an aromatic solvent such as one from the SOLVESSO® series does not afford full solubility and stability to low temperature at the desired active ingredient concentration. These active ingredients preferably include related dinitroaniline herbicides such as benfluralin and butralin; synthetic pyrethroid insecticides such as deltamethrin, lambda- and gamma-cyhalothrin, alpha- and zeta-cypermethrin; other diphenylether herbicides such as aclonifen; phenoxypropionate herbicides such as metamifop; organophosphate insecticides such as phosmet and omethoate; and various acaricides including amitraz, buprofezin and pyridaben.

The agrochemical formulations of the present invention may be applied to plant leaves as foliar sprays, or to plant shoots and to the surrounding soil. Such formulations may also be applied to animals, either topically, orally or as injectables. The formulations may also be applied directly to insects, fungi, molluscs, nematodes and helminths, or to wood and wood products as a component of mixtures applied as coatings for buildings, insect protection nets and so on.

The solution comprising the active ingredient/s dissolved in the primary solvent system is preferably formulated as an EC formulation, or as an EW formulation made from such a concentrate. In order to make an emulsifiable concentrate EC formulation, other additives such as emulsifiers and stabilisers are preferably used. Such additives may add or subtract from the total solubility level of the active ingredient/s depending upon what is used. For example, surfactant emulsifiers containing a salt of dodecylbenzene sulphonate, such as the calcium salt or one or more amine salts, preferably contain additional solvents, like short chain alcohols which enhance overall solubility. However, in other situations, the addition of emulsifiers may dilute the total level of the active ingredient in the formulation.

In order to prepare a preferred EC formulation, the one or more active ingredients is/are dissolved in a combination of benzyl acetate and substantially water-immiscible co-solvent combination, surfactant emulsifiers are added in the range 3-20% w/v and the formulation made up to the required volume. Optionally, prior to making the formulation up to the required volume, one or more further co-solvents, which may be substantially water-miscible or partially water-miscible, may be added. Such optional solvents preferably include, but are not limited to, a cyclic hydrocarbon/s such as cyclohexanone and isopherone; mono-alkylene carbonates, such as ethylene, propylene and butylene carbonates; or dibasic esters.

Emulsifiers for the EC formulations preferably include, but are not limited to, non-ionic surfactants, such as alkoxylated alcohols and alkoxylated alkylphenols; ethoxylated fatty acids; ethoxylated vegetable oils such as ethoxylated castor oil; ethoxylated tristyrylphenol: fatty acid esters of sorbitol and ethoxylated derivatives thereof; ethoxylated amines, and condensates of glycerol. Anionic surfactants such as salts of sulphonated dodecylbenzene and other alkylbenzenes in the range $C_{11}$-$C_{16}$ and salts thereof; alkylether sulphates; and ether phosphates including alkyletherphosphates; alkylphenoletherphosphates; or combinations thereof; salts of phosphate esters of ethoxylated tristyrylphenol and salts of sulphated ethers of ethoxylated tristyrylphenol, can be used as emulsifiers. Catanionic systems, where a cationic amine is present in combination with an alkylsulphonate, an alkylethersulphonate, an ether sulphate or an ether phosphate such as alkyletherphosphate, are also useful.

The emulsifiers for EC formulations can be selected from the group of castor oil ethoxylates, in particular TERMUL® 1284 emulsifier; alkoxylated alcohols, in particular TERMUL® 5459 emulsifier; alkoxylated alkylphenols, in particular TERMUL® 200 emulsifier; ethoxylated amines, in particular TERWET® 3784 and TERIC® 16M15 emulsifiers; ethoxylated tristyrylphenol, in particular TERMUL® 3150 emulsifier; alcohol ethoxylates in particular TERIC® 12A7, 13A9 and 17A2 emulsifiers; fatty acid ethoxylates such as TERIC® OF6 emulsifier; sorbitan ester ethoxylates, such as ECOTERIC® T85 emulsifier; a sulphosuccinate, such as TERMUL® 3665 emulsifier, amine and calcium salts of dodecylbenzene sulphonate, such as the NANSA® EVM range of products; salts of phosphate esters of ethoxylated tristyrylphenol, in particular TERSPERSE® 2202; salts of sulphated ethers of ethoxylated Tristyrylphenol, in particular TERSPERSE® 2218; all of which are available from Huntsman Corporation.

The EC formulation upon dilution provides a stable emulsion free of crystallisation for a sufficient time period, preferably at least two hours, for convenient use. Such emulsion stability is usually determined visually by measuring the amount of cream or sediment which forms in a diluted solution of the active ingredient after the required time period. The tests required to determine the internationally acceptable standards for stability of EC formulations may be found in the Handbooks as provided by the Collaborative International Pesticides Analytical Council (CIPAC). A typical test method used would be CIPAC MT36.3. The internationally acceptable standard of emulsion stability, as determined by the CIPAC methods, for various active ingredients are provided by the Food and Agriculture Organization of the United Nations (FAO) and may be found in the various technical monographs prepared by them.

The use of benzyl acetate together with substantially water-immiscible co-solvents in EC formulations of the present invention is demonstrated with reference to the following non-limiting Examples.

EXAMPLES

Cold Storage Stability

Example formulations were seeded with at least one crystal of the active ingredient being investigated and stored at 0° C. for 7 days as per the cold storage stability testing methodology outlined in CIPAC MT39.1 (CIPAC Volume F, p 128). On completion of the 7-day storage, formulations were assessed for visible signs of crystal growth.

Accelerated Storage Stability

Example formulations were stored at 54° C. for 14 days per the accelerated storage stability testing methodology outlined in CIPAC MT46.1.3 (CIPAC Volume F, p 150). On completion of the 14-day storage, the formulations were assessed for stability paying particular note to sedimentation and/or separation.

Emulsion Stability Test

Example formulations were evaluated according to CIPAC MT36.1.1 (CIPAC volume F, p 108) at ambient temperature. The volume percent of cream after 0.5, 1, 2, and 24 hours was observed and recorded for a 5 in 100 parts dilution. The emulsion tubes were subsequently inverted 10 times and a final reassessment was made at 24.5 hours.

The primary purpose of the emulsion test in this instance is to look for the development of crystals upon dilution. As a result, no effort was made to fully optimize the emulsion performance with respect to cream and oil separation.

600 g/l Trifluralin

| Formulation | g/L |
|---|---|
| Trifluralin | 600 |
| NANSA ® EVM 70/2E | 21.2 |
| NANSA ® SSA | 2.4 |
| TERMUL ® 203 | 44.0 |
| TERWET ® 3784 | 12.0 |
| Solvent | to volume (1 Litre) |

Example 1

In an appropriately sized beaker, 600 g/L of trifluralin was weighed, followed by the addition of 44 g/L of TERMUL® 203, 21.2 g/L of NANSA® EVM 70/2E, 2.4 g/L of NANSA® SSA and 12 g/L of TERWET® 3784. The formulation was then made to volume with an 80:20 blend of benzyl acetate/Solvesso® 150, and stirred over moderate heat (approx. 60° C.) for 15 minutes until homogenous.

Example 2 (Comparative Example)

As for Example 1, the formulation was made up to volume with Solvesso® 200, and then stirred over moderate heat (approx. 60° C.) for 15 minutes until homogenous.

Storage Stability Results

| Appearance | Example 1 | Example 2 |
|---|---|---|
| Initial | Clear, orange, homogenous solution | Clear, orange, homogenous solution |
| Post-storage (7 days at 0° C., seeded) | Clear, orange solution with crystals. Crystals soluble on thawing.[1] | Clear, orange solution with crystals. Crystals soluble on thawing.[2] |
| Post-storage (2 weeks at 54° C.) | Clear, orange homogenous solution | Clear, orange, homogenous solution |

[1]Crystals completely re-dissolved on thawing for 1 hour at ambient temperature.
[2]Crystals completely re-dissolved on thawing for 5 hours at ambient temperature Emulsion Stability Results

| Water Hardness (ppm) | Ease of Bloom | Dispersion in water | Initial | ½ hour | 1 hour | 2 hours | 24 hours | 24.5 hours |
|---|---|---|---|---|---|---|---|---|
| Example 1 | | | | | | | | |
| 20 | Excellent | Excellent | Homogenous, thick yellow emulsion | trace bottom cream | trace bottom cream | 1.8 ml bottom cream | 2.5 ml bottom cream, specs of non-crystalline residue | Nil cream/oil |
| 342 | Excellent | Excellent | Homogenous, thick yellow emulsion | trace bottom cream | trace bottom cream | 2.0 ml bottom cream | 2.8 ml bottom cream, specs of non-crystalline residue | trace bottom cream |
| 1026 | Excellent | Excellent | Homogenous, thick yellow emulsion | 0.3 ml bottom cream | 0.2 ml bottom cream | 0.8 ml bottom cream | 1.7 ml bottom cream, specs of non-crystalline residue | 0.2 ml bottom cream |
| Example 2 | | | | | | | | |
| 20 | Excellent | Excellent | Homogenous, thick yellow emulsion | 0.3 ml bottom cream | 0.5 ml bottom cream | 1.0 ml bottom cream | 2.5 ml bottom cream, crystallisation present | 0.2 ml bottom cream |
| 342 | Excellent | Excellent | Homogenous, thick yellow emulsion | 0.1 ml bottom cream | 0.3 ml bottom cream | 0.9 ml bottom cream | 2.1 ml bottom cream, crystallisation present | 0.1 ml bottom cream |
| 1026 | Excellent | Excellent | Homogenous, thick yellow emulsion | 0.1 ml bottom cream | 0.2 ml bottom cream | 0.4 ml bottom cream | 1.7 ml bottom cream, trace oil, crystallisation present | 0.3 ml bottom cream |

It will be clear from the above Examples that only Example 1 comprising benzyl acetate used in combination with aromatic solvent achieved better overall stability, firstly, in regard to faster dissolution of crystals upon thawing of the concentrate after cold temperature storage, and secondly, in regard to a lack of crystal formation upon dilution of the concentrate in water to form the emulsion.

100 g/L Deltamethrin

| Formulation | g/L |
|---|---|
| Deltamethrin (98%) | 100 |
| NANSA ® EVM 70/B | 15 |
| TERIC ® N13 | 35 |
| Solvent | to volume (1 Litre) |

Example 3

In an appropriately sized beaker, 100 g/L of Deltamethrin was weighed, followed by the addition of 15 g/L of NANSA® EVM 70/2E and 35 g/L of TERIC® N13. The formulation was made to volume with an 80:20 blend of benzyl acetate/Solvesso® 150, and then stirred over moderate heat (approx. 60° C.) for 15 minutes until homogenous.

Example 4 (Comparative Example)

As for Example 4, the formulation was made to volume with xylene, and then stirred over moderate heat (approx. 60° C.) for 15 minutes until homogenous.

Example 5 (Comparative Example)

As for Example 4, the formulation was made to volume with Solvesso® 150, and then stirred over moderate heat (approx. 60° C.) for 15 minutes until homogenous.

Storage Stability Results

| Appearance | Example 3 | Example 4 | Example 5 |
|---|---|---|---|
| Initial | Clear, yellow, homogenous solution | Clear, yellow, homogenous solution | Clear, yellow, homogenous solution |
| Post-storage, seeded at 0° C. for 7 days | Clear, yellow solution with no crystal growth | Clear, yellow solution with crystal growth. Crystals soluble on thawing | Clear, yellow solution with no crystal growth |

-continued

| Appearance | Example 3 | Example 4 | Example 5 |
|---|---|---|---|
| Post-storage at 54° C. for 2 weeks | Clear, yellow, homogenous solution | Clear, yellow, homogenous solution | Clear, yellow, homogenous solution |

Emulsion Stability Results

| Water Hardness (ppm) | Ease of Bloom | Dispersion in water | Initial | ½ hour | 1 hour | 2 hours | 24 hours | 24.5 Hours |
|---|---|---|---|---|---|---|---|---|
| Example 3 | | | | | | | | |
| 20 | Poor | Excellent | Homogenous, thick white emulsion | 2.2 ml bottom cream | 3.2 ml bottom cream | 4.0 ml bottom cream | 6.7 ml bottom cream, trace oil, no crystals | 2.0 ml bottom cream |
| 342 | Poor | Excellent | Homogenous, thick white emulsion | 2.2 ml bottom cream | 3.3 ml bottom cream | 3.9 ml bottom cream | 5.8 ml bottom cream, trace oil, no crystals | 1.8 ml bottom cream |
| 1026 | Poor | Excellent | Homogenous, thick white emulsion | 1.6 ml bottom cream | 2.5 ml bottom cream | 3.8 ml bottom cream | 6.0 ml bottom cream, trace oil, no crystals | 1.8 ml bottom cream |
| Example 4 | | | | | | | | |
| 20 | Good | Excellent | Homogenous, thick white emulsion | 5 ml top cream | 6 ml top cream | 6 ml top cream | 6 ml top cream, coarse crystals present | 5 ml top cream |
| 342 | Good | Excellent | Homogenous, thick white emulsion | 4 ml top cream | 4 ml top cream | 5 ml top cream | 7 ml top cream, trace crystals present | 3 ml top cream |
| 1026 | Good | Excellent | Homogenous, thick white emulsion | 3 ml top cream | 4 ml top cream | 4.2 ml top cream | 5.2 ml top cream, trace crystals present | 2 ml top cream |
| Example 5 | | | | | | | | |
| 20 | Poor | Excellent | Homogenous, thick white emulsion | 2.4 ml bottom cream | 3.9 ml bottom cream | 5.1 ml bottom cream | 6.2 ml bottom cream, coarse crystals, oil | 1.8 ml bottom cream |
| 342 | Poor | Excellent | Homogenous, thick white emulsion | 2.8 ml bottom cream | 4.1 ml bottom cream | 6.1 ml bottom cream | 6.1 ml bottom cream, coarse crystals, oil | 2.2 ml bottom cream |
| 1026 | Poor | Excellent | Homogenous, thick white emulsion | 3.5 ml bottom cream | 6.9 ml bottom cream | 7.1 ml bottom cream | 6.4 ml bottom cream, coarse crystals, oil | 3.5 ml bottom cream |

It will be clear from the above Examples that only Example 3, comprising benzyl acetate in combination with aromatic solvent, achieved stability with regard to a lack of crystallisation in both the concentrate formulation upon cold temperature storage and upon dilution to form the emulsion.

150 g/L Bifenthrin

| Formulation | g/L |
|---|---|
| Bifenthrin (98%) | 150 |
| TERMUL ® 3150 | 150 |
| TERIC ® 13A9 | 100 |
| Solvent | to volume (1 Litre) |

Example 6

In an appropriately sized beaker, 150 g/L of Deltamethrin was weighed, followed by the addition of 150 g/L of TERMUL® 3150 and 100 g/L of TERIC® 13A9. The formulation was made to volume with benzyl acetate, and then stirred over moderate heat (approx. 60° C.) for 15 minutes until homogenous.

Example 7

As for Example 6, the formulation was made to volume with a 80:20 blend of benzyl acetate/Solvesso® 150, and then stirred over moderate heat (approx. 60° C.) for 15 minutes until homogenous.

Example 8 (Comparative Example)

As for Example 6, the formulation made to volume with Solvesso® 150, and then stirred over moderate heat (approx. 60° C.) for 15 minutes until it was homogenous.

Storage Stability Results

| Appearance | Example 6 | Example 7 | Example 8 |
|---|---|---|---|
| Initial | Clear, yellow, homogenous solution | Clear, yellow, homogenous solution | Clear, yellow, homogenous solution |
| Post-storage, seeded at 0° C. for 7 days | Clear, yellow, homogenous solution | Clear, yellow, homogenous solution | Hazy, crystals not obvious. Homogeneous on thawing |
| Post-storage at 54° C. for 2 weeks | Clear, yellow, homogenous solution | Clear, yellow, homogenous solution | Clear, yellow, homogenous solution |

Emulsion Stability Results

| Water Hardness (ppm) | Bloom | Ease of Dispersion in water | Initial | ½ hour | 1 hour | 2 hours | 24 hours | 24.5 Hours |
|---|---|---|---|---|---|---|---|---|
| | | | | Volume (ml) creaming/oil with elapsed time | | | | |
| | | | Example 6 | | | | | |
| 20 | Excellent | Excellent | Homogenous, thick white emulsion | Nil cream/oil | Nil cream/oil | Nil cream/oil | Nil cream/oil, no crystals | Nil cream/oil |
| 342 | Excellent | Excellent | Homogenous thick white emulsion | Nil cream/oil | Nil cream/oil | Nil cream/oil | Nil cream/oil, no crystals | Nil cream/oil |
| 1026 | Excellent | Excellent | Homogenous, thick white emulsion | Nil cream/oil | Nil cream/oil | Nil cream/oil | Nil cream/oil, no crystals | Nil cream/oil |
| | | | Example 7 | | | | | |
| 20 | Excellent | Excellent | Homogenous, thick white emulsion | Nil cream/oil | Nil cream/oil | Nil cream/oil | Nil cream/oil, no crystals | Nil cream/oil |
| 342 | Excellent | Excellent | Homogenous thick white emulsion | Nil cream/oil | Nil cream/oil | Nil cream/oil | Nil cream/oil, no crystals | Nil cream/oil |
| 1026 | Excellent | Excellent | Homogenous, thick white emulsion | Nil cream/oil | Nil cream/oil | Nil cream/oil | Nil cream/oil, no crystals | Nil cream/oil |
| | | | Example 8 | | | | | |
| 20 | Excellent | Excellent | Homogenous, thick white emulsion | Nil cream/oil | Nil cream/oil | Nil cream/oil | Nil cream/oil, coarse crystals | Nil cream/oil |
| 342 | Excellent | Excellent | Homogenous thick white emulsion | Nil cream/oil | Nil cream/oil | Nil cream/oil | Nil cream/oil, trace crystals | Nil cream/oil |
| 1026 | Excellent | Excellent | Homogenous, thick white emulsion | 0.1 ml bottom cream | 0.1 ml bottom cream | 0.1 ml bottom cream | 0.3 ml bottom cream, trace crystals | Nil cream/oil |

It will be clear from the above Examples that both Examples 6 and 7, comprising benzyl acetate used alone or in combination with aromatic solvent, respectively, achieved stability both with regard to a lack of crystallisation in both the concentrate formulation upon cold temperature storage and upon dilution in water to form the emulsion.

It will be appreciated by persons skilled in the art that the present invention is not limited by what has been particularly shown and described hereinabove. Rather, the scope of the present invention includes both combinations and sub-combinations of the features described hereinabove as well as modifications and variations thereof which would be understood by a person of skill in the art upon reading the foregoing description and which are not in the prior art.

Where the terms "comprise", "comprises", "comprised" or "comprising" or the terms "include", "includes", "included" or "including" are used in this specification, they are to be interpreted as specifying the presence of the stated features, integers, steps or components referred to, but not to preclude the presence or addition of one or more other feature, integer, step, component or group thereof.

Further, any prior art reference or statement provided in the specification is not to be taken as an admission that such art constitutes, or is to be understood as constituting, part of the common general knowledge.

The invention claimed is:

1. An agrochemical emulsifiable concentrate (EC) formulation comprising at least one agrochemical active ingredient selected from the group consisting of dinitroaniline herbicides being present at greater than 500 g/L or greater than 50% weight/volume, at least one surfactant emulsifier, a primary solvent system, optionally no more than 10% weight/volume of a non-primary solvent comprising a water-miscible solvent and optionally a stabilizer, wherein the primary solvent system is a combination of benzyl acetate and at least one substantially water-immiscible co-solvent selected from the group consisting of an aromatic hydrocarbon, an aliphatic hydrocarbon, an alkylester, an alkenyl ester, a fatty acid and a fatty acid ester and wherein the weight ratio of benzyl acetate to the substantially water-immiscible co-solvent is in the range of from 10:90 to 90:10.

2. A formulation according to claim 1, wherein the weight ratio of benzyl acetate to the substantially water-immiscible co-solvent is in the range of from 40:60 to 80:20.

3. A formulation according to claim 1, wherein the active ingredient is selected from the group consisting of trifluralin, pendimethalin, butralin, benfluralin and mixtures thereof.

4. A formulation according to claim 3, wherein the active ingredient is trifluralin being present at greater than 500 g/L or greater than 50% weight/volume.

5. A formulation according to claim 1, further comprising one or more substantially water-miscible co-solvents, wherein the water-miscible co-solvent is not required to dissolve the active ingredient.

6. A formulation according to claim 1, wherein the surfactant emulsifier is selected from the group consisting of alkoxylated alcohols, alkoxylated alkylphenols, ethoxylated fatty acids, ethoxylated vegetable oils, ethoxylated tristyrylphenol, fatty acid esters of sorbitol and ethoxylated derivatives thereof, ethoxylated amines, condensates of glycerol, sulfonated alkylbenzenes in the range $C_{11}$-$C_{16}$ and salts thereof, alkylether sulfates, alkyletherphosphates, alkylphenoletherphosphates, salts of phosphate esters of ethoxylated tristyrylphenol, salts of sulfated ethers of ethoxylated tristyrylphenol and a catanionic system, wherein a cationic amine is present in combination with an alkylsulfonate, an alkylethersulfonate, an ether sulfate, or an ether phosphate.

7. A formulation according to claim 6, wherein the stabilizer is present and selected from butylated hydroxytoluene (BHT) and epoxidized soybean oil (ESBO).

8. A formulation according to claim 7, wherein the stabilizer is present in a concentration of up to 3% weight/volume.

9. A formulation according to claim 1, wherein the solvent system is benzyl acetate and an aromatic hydrocarbon.

10. An emulsion-in-water (EW) agrochemical formulation, wherein an agrochemical emulsifiable concentrate (EC) formulation according to claim 1 is further diluted in water to form the EW agrochemical formulation.

11. A method of making an EW formulation according to claim 10, wherein the method comprises the following steps:
 (a) forming a mixture comprising the agrochemical active ingredient, the substantially water-immiscible co-solvent, and benzyl acetate;
 (b) adding the surfactant emulsifier and optionally no more than 10% weight/volume of a water-miscible co-solvent and optionally the stabilizer to form the EC formulation; and
 (c) contacting said EC formulation obtained in step (b) with water to form the EW formulation.

12. A method according to claim 11, wherein step (a) comprises:
 i) forming a mixture comprising the agrochemical active ingredient and benzyl acetate and then adding the substantially water-immiscible co-solvent; or
 ii) forming a mixture comprising the agrochemical active ingredient and the substantially water-immiscible co-solvent and then adding benzyl acetate; or
 iii) forming a mixture comprising the agrochemical active ingredient and a combination of benzyl acetate and the substantially water-immiscible co-solvent; or
 iv) combining the agrochemical active ingredient, benzyl acetate and the substantially water-immiscible co-solvent.

13. A method of making an EC formulation comprising at least one agrochemical active ingredient selected from the group consisting of dinitroaniline herbicides being present at greater than 500 g/L or greater than 50% weight/volume, wherein the method comprises the following steps:
 (a) forming a mixture comprising the agrochemical active ingredient, a substantially water-immiscible co-solvent, and benzyl acetate; and
 (b) adding a suitable surfactant emulsifier and optionally no more than 10% weight/volume of a non-primary solvent comprising a water-miscible co-solvent and optionally a stabilizer;
wherein the substantially water-immiscible co-solvent is selected from the group consisting of an aromatic hydrocarbon, an aliphatic hydrocarbon, an alkylester, an alkenyl ester, a fatty acid and a fatty acid ester and wherein the weight ratio of benzyl acetate to the substantially water-immiscible co-solvent is in the range of from 10:90 to 90:10.

14. A method of making an EC formulation according to claim 13, wherein step (a) comprises:
 i) forming a mixture comprising the agrochemical active ingredient and benzyl acetate and then adding the substantially water-immiscible co-solvent; or
 ii) forming a mixture comprising the agrochemical active ingredient and the substantially water-immiscible co-solvent and then adding benzyl acetate; or
 iii) forming a mixture comprising the agrochemical active ingredient and a combination of benzyl acetate and the substantially water-immiscible co-solvent; or
 iv) combining the agrochemical active ingredient, benzyl acetate and the substantially water-immiscible co-solvent.

15. A method according to claim 14 or claim 12, wherein step ii) is achieved in the presence of heating up to 60° C.

* * * * *